| United States Patent [19] | [11] Patent Number: 4,867,970 |
|---|---|
| Newsham et al. | [45] Date of Patent: Sep. 19, 1989 |

[54] MOISTURELESS ORAL DRUG DELIVERY FORMULATION AND METHOD FOR PREPARING SAME

[75] Inventors: E. A. Newsham, Derbyshire; Jeffrey W. Forrester; Duncan J. Rowley, both of Merseyside, all of United Kingdom

[73] Assignee: E. R. Squibb & Sons, Inc., Princeton, N.J.

[21] Appl. No.: 52,297

[22] Filed: May 21, 1987

[51] Int. Cl.$^4$ .................. A61K 31/78; C09K 3/00
[52] U.S. Cl. ........................ 424/81; 424/435
[58] Field of Search .................. 424/81, 435

[56] References Cited

U.S. PATENT DOCUMENTS

| 3,029,187 | 4/1962 | Steinhardt et al. | 167/60 |
|---|---|---|---|
| 3,029,188 | 4/1962 | Cyr et al. | 167/60 |
| 3,312,594 | 4/1967 | Cyr et al. | 167/82 |
| 3,984,571 | 10/1976 | Chen | 424/362 |
| 4,540,602 | 9/1985 | Motoyama et al. | 427/213.31 |
| 4,542,020 | 9/1985 | Jackson et al. | 514/31 |

*Primary Examiner*—Joseph L. Schofer
*Assistant Examiner*—Peter F. Kulkosky
*Attorney, Agent, or Firm*—Burton Rodney

[57] ABSTRACT

Oral drug delivery systems are provided formed of compositions which include one or more hydrocolloids solids, such as gelatin, pectin, and sodium carboxymethyl cellulose, and preferably mixtures thereof, which solids contain less than about 5% by weight moisture and preferably comprise less than about 50% by weight of the total formulation; and an ointment base such as mineral oil containing dispersed polyethylene (Plastibase). Such oral drug delivery compositions may be used to deliver to the oral mucosa active ingredients such as steroids, anti-fungal agents, anti-bacterial agents and the like and do not harden even upon prolonged storage or upon filling into containers.

19 Claims, No Drawings

MOISTURELESS ORAL DRUG DELIVERY FORMULATION AND METHOD FOR PREPARING SAME

FIELD OF THE INVENTION

The present invention relates to an oral drug delivery formulation which contains a mixture of solids which includes one or more hydrocolloids, which solids contain less than about 5% moisture, and an ointment base, which formulation has improved resistance to hardening during storage and/or during container filling.

BACKGROUND OF THE INVENTION

Drug delivery systems for delivering drugs to the oral mucosa include tinctures, buccal formulations and ointments. Tinctures are easily applied to oral lesions but may be ingested into the body within a relatively short time after application. Buccal formulations may be retained in the oral cavity for longer periods than tinctures; however, they are usually larger in size and thus uncomfortable to retain in the oral cavity and often cause tissue irritation. In addition, they may be separated from lesions by saliva or other exudate. Conventional ointment formulations may be readily applied. However, in many cases, they also may be readily removed from the oral cavity by mechanical movement of the oral tissue such as during speaking or eating. In addition, conventional ointments may bleed during storage or even after application. Moreover, bleeding of active ingredients from ointments after application to oral lesions may cause active ingredients to be separated from such lesions and carried by saliva to other locations in the oral cavity.

A discussion of prior art patents relating to various drug delivery systems including oral delivery systems and/or oral adhesives follows.

U.S. Pat. No. 3,029,187 to Steinhardt discloses anhydrous adhesive pharmaceutical vehicles specifically designed for adhering active ingredients to the oral mucosa which vehicles are formed of an intimate mixture of gelatin and a topically-acceptable vehicle such as petrolatum, lanolin, benzoinated lard, hydrogenated cotton seed oil, carboxymethyl cellulose, pectin, karaya gum, tragacanth, Irish moss extracts, alginates, polyvinyl pyrrolidone, carbo gum, guar gum and pre-treated water-soluble starch. Active ingredients which may be carried by such vehicles include antiseptics, anesthetics, steroids, hormones and antibiotics.

U.S. Pat. No. 3,029,188 to Cyr et al discloses gelatin oral adhesive pharmaceutical preparations which include an intimate admixture of particulate gelatin with mineral oil containing thickening agent, such as polyethylene, dispersed therein. Cyr et al indicate that portions of the gelatin may be substituted by other gums such as carboxymethyl cellulose, pectin, karaya gum, tragacanth, Irish moss extracts, alginates, polyvinyl pyrrolidone, carob gum, guar gum and pre-treated water-soluble starch.

U.S. Pat. No. 3,312,594 to Cyr et al discloses a long-lasting troche which contains a medicament and equal portions of pectin, gelatin and carboxymethylcellulose; the troche interacts with saliva to dissolve in the mouth to form an adhesive composition which secures and retains the medicament to the oral mucosa.

U.S. Pat. No. 3,984,571 to Chen discloses a liquid carrier for a diagnostic or therapeutic agent which liquid carrier includes a fine particle size hydrocolloid, such as a cellulose ether, suspended in a non-aqueous water-immiscible mobile liquid. When a composition containing the diagnostic or therapeutic agent in the liquid carrier is made to contact a moist surface, the mobile liquid is drained off and the hydrocolloid (carrying the diagnostic or therapeutic agent) attaches itself to the surface.

U.S. Pat. No. 4,542,020 to Jackson et al discloses antifungal suppository formulations which are substantially free of water which include an antifungal agent such as nystatin together with a hydrocolloid, such as sodium carboxymethyl cellulose or hydroxypropylmethyl cellulose and a low melting suppository base.

U.S. Pat. No. 4,540,602 to Motoyama Shimesu et al discloses a process for preparing a pharmaceutical composition containing a solid drug in the form of finely divided particles no greater than 10 microns in diameter, wherein a solid drug which is substantially water-insoluble is dissolved in a low-boiling hydrophobic organic solvent, the resulting solution is emulsified in water in the presence of a water-soluble high molecular weight substance which is hydroxypropyl cellulose, methyl cellulose, hydroxyethyl cellulose, hydroxypropyl methyl cellulose, hydroxypropyl ethyl cellulose, carboxymethyl cellulose sodium salt, alpha-starch, hydroxypropyl starch, pullulan, gum arabic, tragacanth gum, gelatin, polyvinyl alcohol, polyvinyl pyrrolidone and mixtures thereof and water is thereafter removed.

DESCRIPTION OF THE INVENTION

In accordance with the present invention, a long-lasting bioadhesive oral ointment formulation is provided which has improved resistance to hardening during storage and during container filling, and upon absorption of water has excellent retention of water-soluble or water-insoluble medicament at a desired treatment site in the oral cavity and causes no or only minimal tissue irritation. The bioadhesive oral ointment formulation of the invention is formed of one or more water-soluble colloids, containing less than about 5% by weight moisture, preferably having a particle size of less than about 100 $\mu$m (micrometers), which hydrates, becomes adhesive and increases retention time of the medicament at the treatment site and an ointment base composition and optionally a water-soluble or water-insoluble therapeutically active ingredient or medicament.

Thus, in essence, the ointment formulation of the invention is easily applied and soon after application at the desired site releases a hydrophilic polymer or hydrocolloid which adheres to the membranes at the desired site and retains a uniform distribution of medicament at the desired site to provide long-lasting treatment.

The ointment formulation of the invention will include a water-soluble or water-insoluble medicament in an amount within the range of from about 0.01 to about 25% by weight, and preferably from about 0.05 to about 15% by weight, depending upon the particular medicament employed, one or more hydrocolloid solids to impart adhesive qualities, such as gelatin and/or sodium carboxymethyl cellulose and/or pectin, carrageenan or sodium alginate, in an amount within the range of from about 0.5 to about 60% by weight and preferably from about 2 to about 45% by weight, and an ointment base in an amount within the range of from about 25 to about 70% by weight and preferably from about 30 to about 65% by weight, all of the above % being based on the total weight of the ointment formulation.

It is essential that the so-called solids portion of the ointment formulation of the invention, that is, the hydrocolloids to be mixed into the ointment base, has a moisture content of less than about 5% by weight of such solids and preferably less than about 2% by weight of such solids, and optimally a moisture content of zero. It has been unexpectedly found that the less moisture in the hydrocolloid solids, the less chance that there will be premature hardening of the ointment formulation during storage or on filling of tubes or other containers. Furthermore, the tendency of hardening on storage can be further reduced by reducing hydrocolloid solids content, for example, from about 55 to 60% solids down to from about 50 to about 30% solids and preferably down to from about 45 to about 35% solids.

In addition, in a preferred embodiment of the invention, the hydrocolloids will have an average particle size of less than about 100 %m and preferably less than about 70 %m to reduce grittiness.

The medicament which may be employed in the ointment formulation of the invention may be water-soluble or water-insoluble and may include antifungal agents, such as amphotericin B, nystatin, griseofulvin, miconazole, ketoconazole, tioconazole, econazole, clotrimazole, and other macrolide antifungal agents, antibacterials (such as metronidazole, penicillins, monobactams, ampicillin, neomycin, erythromycin, mupirocin, tyrothricin, gramicidin, cephalosporins, gentamycin and other aminoglycosides, anti-cancer agents (such as 5-fluorouracil), anti-inflammatory agents (such as hydrocortisone, other known steroids such as prednisone, prednisolone, triamcinolone, dexamethasone, and betamethasone), hormones (such as oestriol), analgesic and anti-inflammatory agents such as acetaminophen, phenacetin, aspirin, aminopyrine, sulpyrine, phenylbutazone, mefenamic acid, flufenamic acid, Ibufenac, ibuprofen, indomethacin, colchicine, and Probenecid, and anti-viral agents (such as acyclovir, ribavarin, trifluorothyridine or idoxuridine) antiseptics, hexachlorophene, tetramethyl thiuramdisulfide, benzalkonium chloride, thimerosal, hexylresorcinol, cresols, zinc oxide, methylene blue, boric acid, chloramine-T, gentian violet, phenyl mercuric chloride, phenyl mercuric nitrate basic, acriflavin, sodium perborate, metallic peroxides (e.g. sodium peroxide), sodium permanganate, and the halogens. The medicament will be present in an amount within the range of from about 0.01 to about 25% and preferably from about 0.05 to about 15% by weight depending upon the particular medicament employed and the desired site of action.

Ointment formulations containing such medicaments in accordance with the present invention may be administered up to two times per day or any convenient regimen.

The hydrophilic polymers or hydrocolloids or solids portion which may be present in the ointment formulation of the invention is formed of water-swellable polymeric substances such as cellulosic polymers and gums. The hydrocolloid will preferably comprise gelatin, pectin, cellulose polymers which are cellulose ethers such as methyl cellulose, cellulose alkyl hydroxylates such as hydroxymethylpropyl cellulose, hydroxypropyl cellulose, hydroxymethyl cellulose or hydroxyethyl cellulose, cellulose alkyl carboxylates such as carboxymethyl cellulose and carboxyethyl cellulose, and alkali metal salts of cellulose alkyl carboxylates, such as sodium carboxymethyl cellulose and sodium carboxyethyl cellulose, or acrylic acid homo- or copolymers or alkali metal salts thereof.

It is to be understood that other known hydrocolloids may be employed in the present invention, including, for example, gum acacia, carrageenan, guar gum, gum tragacanth, gum xanthan, ammonium or sodium alginate or mixtures thereof.

Preferably the solids component, namely, the hydrocolloids, are a mixture of gelatin, sodium carboxymethyl cellulose and pectin, wherein the gelatin is present in an amount within the range of from about 0.5 to about 60% and preferably from about 5 to about 40% by weight of the hydrocolloid mixture, the pectin is present in an amount within the range of from about 0.5 to about 60% and preferably from about 5 to about 40% by weight of the hydrocolloid mixture, and the sodium carboxymethyl cellulose is present in an amount within the range of from about 0.5 to about 60% and preferably from about 5 to about 40% by weight of the hydrocolloid mixture.

Thus, the sodium carboxymethyl cellulose will be employed in a weight ratio to the gelatin of within the range of from about 0.008:1 to about 120:1 and preferably from about 0.125:1 to about 8:1 and the sodium carboxymethyl cellulose will be employed in a weight ratio to the pectin of within the range of from about 0.008:1 to about 120:1 and preferably from about 0.125:1 to about 8:1.

Preferably, the hydrocolloids solids component will contain less than 2% by weight moisture and optimally 0 to 1% by weight moisture and will be employed in a weight ratio to the ointment base of within the range of from about 0.05:1 to about 3:1 and preferably from about 0.43:1 to about 1.5:1.

The ointment base suitable for use herein may comprise any conventional ointment formulation suitable for use in the oral cavity, such as disclosed in Remington's "Pharmaceutical Sciences," Sixteenth Edition (Mack Publishing Co., Pa.). Preferred ointment base formulations are set out in U.S. Pat. Nos. 3,029,188 and 2,628,187 and comprise mineral oil containing a thickening agent, such as polyethylene, dispersed therein. The thickening agent will be present in an amount of from about 0.25 to about 50% of the combined weight of mineral oil and thickening agent.

The oils which may be used and which are embraced within the term "mineral oil" as used herein are the oils which are liquid at any temperature in the range from 0° C. to 60° C. and which are essentially hydrocarbons occurring in mineral oil, their distillates and their cracked or polymerized derivatives, an example of the last being polybutene which includes the polymers of butylene and its isomers. The mineral oil may be of any desired character or viscosity, from one which is a thin liquid to one which is so thick that it does not flow at ordinary temperature (20° C.).

Thickening (gelling) agents utilizable for dispersion in the mineral oil include, inter alia paraffin wax, amorphous wax (e.g. microcrystalline wax), ozokerite, animal waxes (e.g. beeswax), vegetable waxes (e.g. castor wax), and hydrocarbon polymers (e.g. polymers of ethylene having an average molecular weight varying from 3,500 to 26,000 and polyisobutylene of a high molecular weight). The preferred thickening agent is polyethylene having a molecular weight of at least 3,500.

A preferred ointment base formulation comprises mineral oil containing polyethylene having a molecular weight of at least 3,500. An example of such an ointment is Plastibase 50W (distributed by E. R. Squibb & Sons, Inc.).

Preferred ointment formulations of the invention are set out below.

| Ingredient | Mg/g.ointment formulation |
|---|---|
| Medicament (For example, triamcinolone acetonide | 0.5 to 150 |
| Hydrocolloids solids (containing less than 2% by weight moisture and having particle size of less than 100 μm) | |
| Sodium carboxymethyl cellulose | 50 to 400 |
| Pectin | 50 to 400 |
| Gelatin | 50 to 400 |
| Ointment base, for example, Plastibase 50W | 300 to 650 |

The ointment formulation of the invention may be prepared as follows.

The hydrocolloid solids component, preferably, sodium carboxymethyl cellulose, pectin and gelatin are screened and then blended together using, for example, a turbula mixer. The blend is then dried (preferably to dryness), for example, by heating the solids as a powder blend in an oven or by microwave or fluid bed drying.

The ointment base, medicament and dried hydrocolloids powder blend are mixed, preferably under vacuum to prevent aeration to form the ointment formulation of the invention.

The oral formulations of the invention will be in the form of homogeneous pastes and will retain their homogeneity without bleeding and will remain flowable (that is, will not unduly harden) even upon prolonged storage or upon filling into tubes. Moreover, the oral formulations of the invention have excellent oral adhesiveness so that upon application to the oral cavity, the formulations are retained for prolonged periods, keeping their original shape at the site of application even after being heated by body temperature, and moistened with saliva. Accordingly, the oral formulations of the invention will maintain its pharmacological efficacy at the site of application without being transferred to other locations in the oral cavity.

The following working Examples represent preferred embodiments of the present invention. Unless otherwise indicated, all temperatures are expressed in degrees Centigrade.

EXAMPLES 1 AND 2

Oral ointment formulations in accordance with the present invention and Control A formulation having the following composition were prepared as described below.

Blends of sodium carboxymethyl cellulose, gelatin and pectin containing 0% (Example 1), 8.95% (Example 2) and 16.6% (Control A) moisture in ointment base were mixed together for 30 minutes at 40 rpm followed by 60 minutes at 25 rpm under vacuum to prevent aeration with a homogeneous ointment was obtained. The composition of each formulation is set out below in Table I.

TABLE I

| | Parts by Weight | | |
|---|---|---|---|
| Ingredient | Example 1 | Example 2 | Control A |
| Hydrocolloid solids | | | |
| NaCMC | 16.67 | 16.67 | 16.67 |
| Pectin | 16.67 | 16.67 | 16.67 |
| Gelatin | 16.67 | 16.67 | 16.67 |
| % moisture in hydrocolloid solids | 0 | 8.95 | 16.6 |
| Plastibase 50W ointment [mineral oil-95% polyethylene-5% M.W. 21,000] | 50 | 50 | 50 |

| | Extrusion energy (Milli-joules (mj)) | | Extrusion energy (mj) | | Extrusion energy (mj) | |
|---|---|---|---|---|---|---|
| | Unexposed | After 4 weeks at 30°/75% RH | Unexposed | After 4 weeks at 30°/75% RH | Unexposed | After 4 weeks at 30°/75% RH |
| Hardening in tubes | 95.7 | 119.8 | 109.4 | 180.2 | 113.9 | 227.3 |
| % Change in hardening | | 25% | | 65% | | 100% |

Each of the ointment formulations were evaluated for tendency to harden in tubes employing the following test.

5 g of the product was packed into tubes, the tubes were crimped, and 20 mm of ointment was squeezed out through the opening. The tubes were stored at 30°/75% relative humidity for 4 weeks in this condition without a cap. In addition, bulk ointment was stored at room temperature in closed glass containers. After the storage period, the product from the tubes was compared with bulk product.

To measure the degree of hardening, product was placed in a glass syringe with a metal plunger. An Instron 1122 was then used to depress the plunger by 6 mm (at 10 mm/min) extruding the product through the syringe nozzle. The energy required to accomplish this was obtained from the Instron integrator.

As seen in Table I, referring to the portions entitled "Hardening in Tubes", and "% change in hardening" the unexposed samples showed an increasing extrusion energy (or increased % hardening) with increasing moisture. The samples exposed and stored at 30°/75% RH showed an increase in required extrusion energy which is greater with increasing moisture content. The ointment prepared containing 16.6% moisture in the hydrocolloids solids (Control A) hardened by 100% (and was barely flowable from the tube container), whereas the ointment product prepared containing 8.95% moisture in the hydrocolloids solds (Example 2) hardened by 65%, but was still flowable from the tube container, while the ointment product prepared containing 0% moisture in the hydrocolloids solids (Example 1) hardened by only 25% and was readily flowable from the tube container.

EXAMPLES 3 AND 4

Oral ointment formulations (Examples 3 and 4) in accordance with the present invention and Control B having the following composition were prepared and tested as described in Examples 1 and 2.

TABLE II

| | Parts by Weight | | |
|---|---|---|---|
| Ingredient | Example 3 | Example 4 | Control B<br>No drying of solids |
| Hydrocolloid solids (% solids) | (40%) | (35%) | (50%) |
| NaCMC | 13.33 | 11.7 | 16.67 |
| Pectin | 13.33 | 11.7 | 16.67 |
| Gelatin | 13.33 | 11.7 | 16.67 |
| % moisture in hydrocolloid solids | 0 | 0 | 18% |
| Plastibase 50W ointment [mineral oil-95% polyethylene-5% M.W. 21,000] | 60 | 65 | 50 |

| | Extrusion energy (Milli-joules (mj)) | | Extrusion energy (mj) | | Extrusion energy (mj) | |
|---|---|---|---|---|---|---|
| | Unexposed | After 4 weeks at 30°/75% RH | Unexposed | After 4 weeks at 30°/75% RH | Unexposed | After 4 weeks at 30°/75% RH |
| Hardening in tubes | 70.1 | 79.7 | 70.2 | 70.4 | 63.1 | 162 |
| % Change in hardening | | 13.6% | | 0.26% | | 158% |

As seen from the above results set out in Table II, hardening appears to have been substantially eliminated employing the Example 4 formulation which includes 35% dried hydrocolloids solids, and hardening was substantially reduced employing the Example 3 formulation which includes 40% dried hydrocolloids solids. However, with the Example 4 formulation, there was a reduction in adhesion although it would still be considered useful as an oral ointment delivery system.

The results for the Control B formulation shows that where the hydrocolloids solids (representing about 50% by weight of the ointment formulation) are untreated so that it contains about 18% moisture, the ointment formulation hardened in the tubes to a state so that it was barely flowable and thus entirely too viscous.

EXAMPLES 5 AND 6

Oral steroid ointment formulations in accordance with the present invention having the following compositions are prepared as described below.

| | Parts by Weight | |
|---|---|---|
| Ingredient | Ex. 5 | Ex. 6 |
| Triamcinolone acetonide | 0.1 | 0.1 |
| Hydrocolloids solids (sodium carboxymethylcellulose, pectin and gelatin (⅓, ⅓, ⅓ mixture containing less than 1% moisture) | 40 | 45 |
| Plastibase 50W ointment [mineral oil-95% polyethylene (M.W. 21,000 - 5%)] | 59.9 | 54.9 |

The sodium carboxymethyl cellulose, gelatin, and pectin (dried for 16 hours in a drying oven at 60° C.) and ointment are mixed together for 30 minutes at 40 rpm followed by 60 minutes at 25 rpm under vacuum to prevent aeration until a substantially homogeneous ointment is obtained. Thereafter, triamcinolone acetonide is added with thorough mixing until a homogeneous ointment paste is obtained.

The so-formed oral steroid ointment formulations are found not to harden even upon prolonged storage or filling into tubes.

EXAMPLE 7

An oral ointment formulation in accordance with the present invention having the following composition using fine grade pectin prepared was described below.

| Ingredient | Amount |
|---|---|
| Initial Mix | |
| Hydrocolloid solids (Powder Blend) | |
| NaCMC | 60 kg |
| Pectin (citrus) USP-L (200 mesh) | 60 kg |
| Gelatin | 60 kg |
| Final Mix | |
| Powder Blend Dried | 120 kg |
| Plastibase 50W ointment | 180 kg |

The hydrocarbon solids were sieved through a 60 mesh screen, transferred to an Artofex planetary mixer, mixed for 15 minutes, transferred to stainless steel trays and dried in a fan-assisted oven at 80° C. for 16 hours to form the dried powder blend.

The dried powder blend was added to the Plastibase in a dough mixer while mixing at slow speed. The mixture was mixed under vacuum for 2 minutes at fast speed and then transferred to stainless steel containers.

The so-formed composition was found to be readily flowable even after prolonged storage and was smooth and elegant without exhibiting grittiness.

What is claimed is:

1. An oral drug delivery system, in the form of an oral ointment formulation, comprising one or more hydrocolloids solids in an amount within the range of from about 0.5 to about 60% by weight of the formulation, containing less than about 5% by weight moisture, and an ointment base therefor, said formulation having resistance to hardening even upon prolonged storage or filling into containers, whereupon application of said formulation at the desired site of action in the oral cavity, moisture in said oral cavity causes said hydrocolloid to swell and medicament to be released and to adhere to and be retained at the desired site of action.

2. The formulation as defined in Claim 1 further including a medicament in an amount within the range of from about 0.01 to about 25% by weight of the total formulation.

3. The formulation as defined in claim 2 wherein the medicament is an antifungal agent.

4. The formulation as defined in claim 3 wherein the antifungal agent is nystatin, clotrimazole, amphotericin B, miconazole, ketoconazole or griseofulvin.

5. The formulation as defined in claim 2 wherein the medicament is a steroid.

6. The formulation as defined in claim 5 wherein said steroid is triamcinolone acetonide.

7. The formulation as defined in claim 1 wherein said hydrocolloid is gelatin, pectin, cellulose ether, a cellulose alkyl hydroxylate, a cellulose alkyl carboxylate, an alkali metal salt of a cellulose alkyl carboxylate, an acrylic acid homo- or copolymer or salt thereof, sodium alginate, carrageenan or mixtures thereof.

8. The formulation as defined in claim 1 wherein said hydrocolloid is a mixture of gelatin, pectin and sodium carboxymethyl cellulose.

9. The formulation as defined in claim 2 wherein said ointment base is mineral oil containing a thickening agent.

10. The formulation as defined in claim 9 wherein said ointment base is mineral oil containing polyethylene.

11. The formulation as defined claim 2 including one or more antifungal agent and/or antibacterial agents as the medicament.

12. The formulation as defined in claim 1 wherein the hydrocolloids solids contain less than 1% by weight moisture.

13. The formulation as defined in claim 1 wherein the hydrocolloids solids are present in an amount within the range of from about 30 to about 50% by weight of the total formulation.

14. The formulation as defined in claim 13 wherein the hydrocolloid is comprised of from about 0.5 to about 60% by weight gelatin, from about 0.5 to about 60% by weight pectin, and from about 0.5 to about 60% by weight sodium carboxymethyl cellulose, said % being based on the weight of the hydrocolloid mixture.

15. The formulation as defined in claim 10 wherein the medicament is triamcinolone acetonide, the ointment base is mineral oil thickened with polyethylene and said hydrocolloids solids is a mixture of gelatin, pectin and sodium carboxymethyl cellulose, said solids containing less than about 1% by weight moisture and being present in a weight ratio to said ointment base of within the range of from about 0.43:1 to about 1:1.

16. The formulation as defined in claim 1 wherein said hydrocolloids have an average particle size of less than about 100 micrometers.

17. A method for preparing an oral drug delivery system in the form of an oral ointment formulation having improved resistance to hardening during storage, as defined in claim 1, which comprises drying the hydrocolloids solids to a moisture content of less than about 5% by weight of said hydrocolloids solids, and mixing the so-dried hydrocolloids solids with said ointment base to form said oral ointment formulation.

18. The method as defined in claim 17 wherein said hydrocolloids solids are dried to about 0% moisture content.

19. The method as defined in claim 17 wherein said hydrocolloids solids are comprised of sodium carboxymethyl cellulose, pectin and gelatin and said ointment base is mineral oil containing polyethylene.

* * * * *